United States Patent [19]

Jahnsen et al.

[11] 4,186,187

[45] Jan. 29, 1980

[54] SAMPLE PROCESSOR FOR THE AUTOMATIC EXTRACTION OF FAMILIES OF COMPOUNDS FROM LIQUID SAMPLES AND/OR HOMOGENIZED SOLID SAMPLES SUSPENDED IN A LIQUID

[75] Inventors: Vilhelm J. Jahnsen, Lake View Terrace; Charles F. Campen, Jr., Arcadia, both of Calif.

[73] Assignee: California Institute of Technology, Pasedena, Calif.

[21] Appl. No.: 445,484

[22] Filed: Feb. 25, 1974

Related U.S. Application Data

[63] Continuation of Ser. No. 274,216, Jul. 24, 1972, abandoned.

[51] Int. Cl.² .................. B01D 15/00; B01D 15/08
[52] U.S. Cl. ............................. 422/64; 422/269; 422/300
[58] Field of Search .......... 23/259, 269, 272.6, 23/272.5, 272, 272 SC

[56] References Cited

U.S. PATENT DOCUMENTS

| | | | |
|---|---|---|---|
| 2,692,820 | 10/1954 | Alway | 23/272 |
| 3,088,714 | 5/1963 | Isreeli | 23/259 X |
| 3,219,416 | 11/1965 | Natelson | 23/259 |
| 3,240,068 | 4/1966 | Horeth | 23/259 X |
| 3,443,905 | 5/1969 | Silver | 23/269 |
| 3,449,959 | 5/1974 | Grimshaw | 23/259 |
| 3,457,048 | 7/1969 | Stephens | 23/259 |
| 3,536,450 | 10/1970 | Dus | 23/259 |
| 3,561,932 | 2/1971 | Gruverman | 23/272 |
| 3,594,129 | 7/1971 | Jones | 23/259 |

FOREIGN PATENT DOCUMENTS

| | | | |
|---|---|---|---|
| 1176611 | 8/1964 | Fed. Rep. of Germany | 23/269 |
| 1118592 | 3/1956 | France | 23/272.5 |
| 1365691 | 7/1963 | France | 23/269 |

*Primary Examiner*—Stephen J. Emery
*Attorney, Agent, or Firm*—Freilich, Hornbaker, Wasserman, Rosen & Fernandez

[57] ABSTRACT

A sample processor and method for the automatic extraction of families of compounds, known as extracts, from liquid and/or homogenized solid samples are disclosed. The sample processor includes a tube support structure which supports a plurality of extraction tubes, each containing a sample from which families of compounds are to be extracted. The support structure is moveable automatically with respect to one or more extraction stations, so that as each tube is at each station a solvent system, consisting of a solvent and reagents, is introduced therein. As a result an extract is automatically extracted from the tube. The sample processor includes an arrangement for directing the different extracts from each tube to different containers, or to direct similar extracts from different tubes to the same utilization device.

9 Claims, 13 Drawing Figures

SAMPLE PROCESSOR FOR THE AUTOMATIC EXTRACTION OF FAMILIES OF COMPOUNDS FROM LIQUID SAMPLES AND/OR HOMOGENIZED SOLID SAMPLES SUSPENDED IN A LIQUID

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

This is a continuation, of application Ser. No. 274,216, filed July 24, 1972, now abandoned.

BACKGROUND OF THE INVENTION

1. Field of the Invention

The present invention generally relates to chemical compound processing and, more particularly, to a system for, and method of, automatically extracting families of chemical compounds from liquid and/or homogenized solid samples.

2. Description of the Prior Art

At present various techniques are employed to separate families of chemical compounds, generally referred to as extracts, from liquid samples or from homogenized solid samples, suspended in a liquid. For explanatory purposes to simplify the following description all such samples may generally be referred to as liquid samples, or simply, samples. Those techniques require the performance of a significant number of steps by trained technicians. Consequently the cost and time of extraction are quite high. With the ever-increasing requirements for very large numbers of extractions in various laboratories, such as those engaged in the fields of clinical chemistry, forensic studies, and quality control, a need exists for a system and method which would simplify the extraction process and thereby reduce both processing time and cost. This can be achieved by automating the processing of liquid samples to obtain extracts therefrom, thereby relieving trained technicians from having to perform such tasks manually.

OBJECTS AND SUMMARY OF THE INVENTION

It is a primary object of the present invention to provide a system for processing liquid and/or homogenized solid samples to obtain extracts therefrom which requires minimum operator attendance.

Another object of the invention is to provide a sample processor for automatically obtaining extracts from liquid samples.

A further object of the present invention is to provide a novel relatively inexpensive sample processor which is easily adapted to obtain automatically one or more extracts from each of a large number of liquid samples speedily and economically.

Yet another object of the invention is to provide an automatic method of obtaining extracts from liquid samples which requires only a minimum of operator attendance.

Yet a further object is to provide a new method of automatically obtaining one or more extracts from each of a plurality of liquid samples so as to reduce overall time and/or cost of extraction.

These and other objects of the invention are achieved by providing a sample processor in which each sample is adsorbed by an adsorbent packing material in a different extraction tube. One or more extracts are obtained from each sample by the successive introduction of different solvent systems into the tube. Each solvent system includes a solvent and reagents which when passing through the packing material move a particular family of compounds in the adsorbed sample across the liquid/solvent phase boundary so that as the solvent exits the tube it carries the desired extracts, which are dissolved therein. The novel sample processor includes a tube support structure which supports all the extraction tubes containing the adsorbed samples. It also includes one or more dispensing heads through which solvent systems are dispensed. The tube support structure is stepped automatically relative to the dispensing heads so that at each position solvent systems are directed from the heads into different tubes. As a result, extract-containing solvents are automatically eluted from the tubes receiving the solvent systems. Receiving means are provided to receive the extracts exiting the various tubes. The latter may comprise one or more extract containers associated with each tube and supported on an automatically steppable container support structure so that as each extract exits a tube, one of the containers associated therewith is positioned to receive the extract. The receiving means may comprise an arrangement for successively receiving similar extracts from the different tubes and continuously direct them to an appropriate utilization device. In the latter a washing solution is passed between successive extracts to prevent cross-contamination.

The novel features of the invention are set forth with particularity in the appended claims. The invention will best be understood from the following description when read in conjunction with the accompanying drawings.

DETAILED DESCRIPTION OF THE PREFERRED EMBODIMENTS

Figure 1:
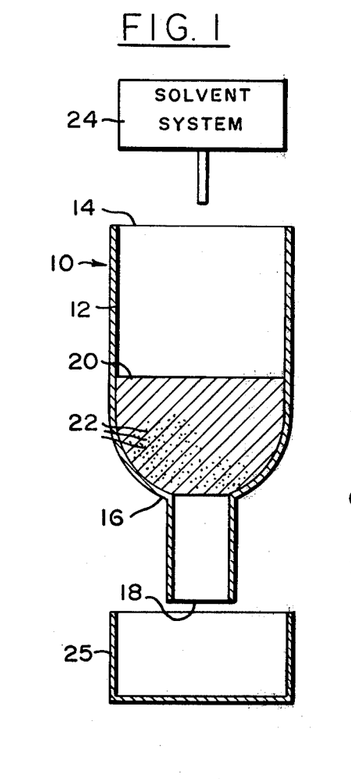
FIG. 1 is a cross-sectional view of the type of extraction tube used in the present invention.

The present invention makes use of an extraction tube which enables the extraction of one or more extracts from a liquid sample held therein, by passing one or more solvent systems therethrough. Thus, before describing the present invention the extraction tube will be described first in connection with FIG. 1. Therein an extraction tube 10 is shown, consisting of a hollow cylinder 12 which extends from an open end 14 to an opposite end 16. The latter is funnel-shaped, terminating in an open nozzle 18. When the tube is disposed vertically, as shown in FIG. 1, in the absence of any adsorbing material in the tube any liquid introduced through open end 14, which serves as the input end, would flow and exit through nozzle 18.

In the tube an inert or chemically active or combination of adsorbent packing materials 20 fills a portion of the cylinder 12 near end 16. The function of material 20 is to adsorb thereunto any liquid, whether aqueous or non-aqueous, in which the sample is dissolved or homogenized and which is introduced into the tube 10 through input end 14. Material 20 adsorbs the liquid and prevents it from flowing out through nozzle 18. As will be pointed out hereafter, the amount of packing material is chosen to insure that all the liquid in which the sample is dissolved is adsorbed by the material 20.

In use, the liquid, in which the sample containing various chemical compounds is dissolved, is first introduced into the tube 10 through end 14. When coming in contact with material 20 the sample-containing liquid is adsorbed by material 20. Thus, the latter keeps the sample in a fixed position in the tube for extraction purposes. In FIG. 1 dot 22 designates the adsorbed liquid sample. To extract any particular family of compounds, herein referred to as an extract, from the adsorbed sample a particular solvent system (SS) from an appropriate source 24 is introduced into the tube through end 14. Generally, the solvent system is a mixture of reagents and a solvent which is immiscible in the adsorbed liquid. The reagents are chosen so that as the solvent system passes through the material 20 they leach our or desorb the desired extract from the sample while the rest of the sample remains adsorbed by the materal 20. Alternately stated, the reagents are chosen to remove the desired extract from the adsorbed liquid phase to the solvent phase. The desired extract dissolves in the non-adsorbed solvent and exits therewith through nozzle 18. Any appropriate container such as container 25 may be positioned below the nozzle 18 to receive the solvent with the desired extract dissolved therein.

The packing material 20 is chosen to insure the proper adsorption of the liquid sample over a large adsorbing surface area and to provide sufficient void to enable the solvent with the extract to pass therethrough. Hereafter to simplify the description the solvent which exits the tube with the extract into container 25 will simply be referred to as the extract. As the solvent system passes through the material 20 since the liquid with the sample is adsorbed over a large surface area optimum liquid-liquid interface is achieved enabling the reagents to remove the desired extract from the liquid phase to the solvent phase.

As is appreciated, compounds can be extracted from a sample dissolved in an aqueous solution with reagents which adjust the pH value of the sample so that certain compounds become deionized while the remaining ionized compounds remain in the aqueous solution. In the present invention, the reagents of each solvent system are chosen to adjust the pH value of the adsorbed sample to a particular value in order to deionize or desorb a particular extract, while the rest of the sample's compounds remain ionized and adsorbed by material 20.

If the sample contains different families of compounds and it is desired to extract several extracts therefrom once the first extract is extracted another extract may be extracted from the sample, remaining in the tube 10. This may be achieved by introducing a second solvent system containing different reagents to extract a different extract which is dissolved in the system's solvent and which exits therewith through nozzle 18 into a second container.

Various presently known adsorbing materials are suitable as material 20. These include ceramic wool, which is a form of glass wool, filter paper either, shredded or beaded cellulose beads or surgical grade cotton. The amount of, or volume occupied by, the material 20 depends on the volume of the sample-containing liquid which is to be adsorbed thereby. The density with which material 20 is packed in the tube should be sufficient to insure the complete adsorption of the sample-containing liquid, yet provide sufficient void or spacing to enable the non-adsorbed solvent to pass therethrough. The solvent and the reagents i.e., each solvent system depends on the properties of the sample-containing liquid and the extract extracted from the sample therein.

In one embodiment, actually reduced to practice, the tube comprises a hollow glass cylinder with an inner diameter (I.D.) of 23 mm and 135 mm long. The packing material consists of a ceramic wool, sold by the Carborundum Co. under the name Fiberfrax Paper, which is available in roll form. Strips of this material 17 inches long are rolled up in the cylinder 12. For liquid samples of about 10 to 20 ml strips 4 inches wide are used, while for samples of less than 5 ml strips of about 1.5 inches wide are employed.

The extraction tube was used most successfully to extract several different extracts, comprising different families of compounds, from aqueous solutions. From each sample up to three different extracts were extracted successively by successively passing through the tube three different solvent systems. These included a first extract of acidic and neutral compounds, a second extract of amphoteric compounds and a third extract of basic compounds.

In operation after adsorbing the sample on material 20 a first solvent system, 60 ml in volume, was injected into the tube. The first solvent system (SSI) consisting of a mixture of methylene chloride or chloroform and glacial acetic acid at a ratio of 99.75:0.25 adjusted the adsorbed-sample pH to a value of about 4. Consequently, the acidic compounds become deionized and exited as did the neutral compounds as an extract with the non-adsorbed methylene chloride solvent. However, all the rest of the compounds remained ionized and adsorbed by materail 20. Thereafter, 60 ml of a second solvent system (SSII) consisting of a mixture of methylene chloride, methanol and ammonium hydroxide at a ratio of 90:9.5:0.5 was introduced. It adjusted the pH to a value of about 8.5, to leach out the second extract of the amphoteric compounds. Following such extraction a third solvent system (SSIII) of methylene chloride; methanol and ammonium hydroxide at a ratio of 90:9.0:1.0 was injected into the tube. It adjusted the pH value to 12 thereby extracting the third extract of the basic compounds.

Since the extraction tube enables the extraction of one or more extracts from a sample by the successive introduction of one or more solvent systems into the tube and the successive retrieval of one or more extracts, which exit the tube nozzle, it has been discovered that the entire extraction process can be performed automatically by any one of a plurality of embodiments of a novel sample extraction system, hereafter also referred to as the sample processor, and thereby greatly reduce both the time and cost of extraction. In accordance with the present invention, in order to extract a single extract from each of a plurality of samples, a plurality of extraction tubes are simultaneously supported on a support structure. Each tube has adsorbed therein a different sample. Also provided is a dispensing head which is connected to an appropriate source of solvent system through a conduit and a pump so that controlled amounts of solvent system may be dispensed through the head. The support structure is moved with respect to the head so that as each extraction tube is under the head a fixed predetermined quantity of solvent system is injected into the tube. Associated with each extraction tube is an extract container. All the containers are supported on a different support structure. The latter moves so that whenever any of the extraction tubes is positioned under the dispensing head, and solvent system is injected thereinto, the container associated with the tube is under the tube's nozzle and is in position to receive the extract which exits the tube's nozzle.

Figure 2:
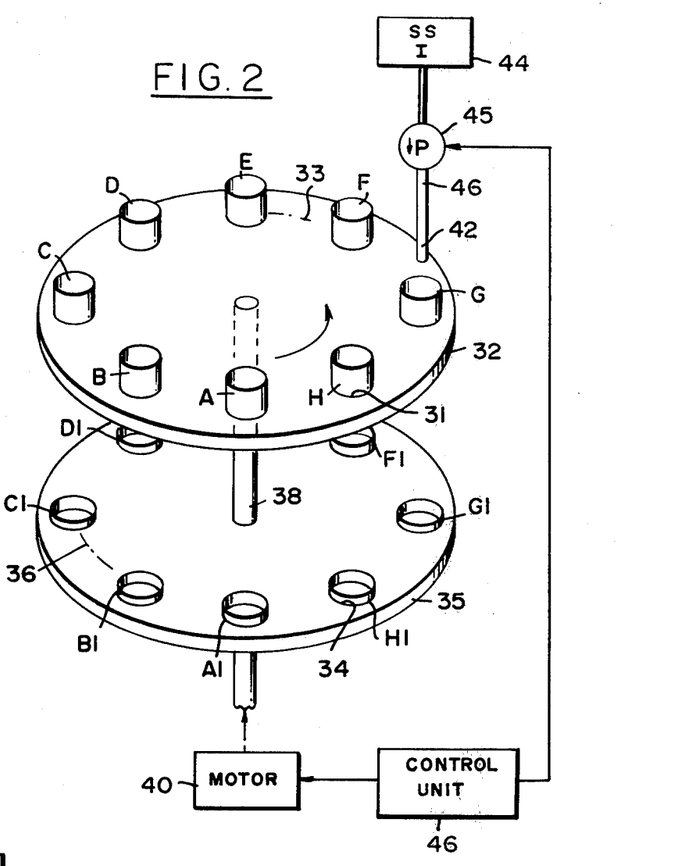
FIGS. 2-6 are diagrams of five different embodiments of the invention.

Such an arrangement is shown in FIG. 2 in which A through H designate eight extraction tubes supported in apertures 31 in a rotatable plate 32. The apertures 31 are equidistantly located along a circular line 33. Although only eight tubes are shown for explanatory purposes only, any number of tubes may be supported on plate 32. Associated with extraction tubes A through H are eight extract containers A1–H1 respectively, which are supported in apertures 34 in a second rotatable plate 35 along a similar circular line 36. The two plates 32 and 35 are mounted, with plate 35 below plate 32, on a shaft 38 which is rotatably steppable by a stepping motor 40. The plates are mounted so that each extract container is at all times positioned just below the output nozzle of its associated extraction tube.

Also included is a dispensing head 42, located above the plate 32, and connected to a source 44 of a solvent system, designated SSI, through a pump 45 and conduit or pipe line 46. The function of the pump, when activated, is to pump solvent system at a predetermined rate during a preselected period to the dispensing head 42. Thus, whenever pump 45 is activated a fixed quantity of the solvent system is dispensed through head 42. The operation of both motor 40 and pump 45 are controlled by a control unit 46.

In operation the motor 40, by means of shaft 38, steps the two plates so that at each stepped position one of the extraction tubes is below the dispensing head 42 and above its associated extract container. Then pump 45 is activated to dispense the preselected quantity of solvent system at a constant rate into the extraction tube, such as tube G shown in FIG. 2. As the solvent system passes through the adsorbing material on which the liquid sample is adsorbed, extraction takes place and the extract exits through the tube's nozzle. The extract is automatically collected in extract container G1, which is below the nozzle of tube G. Thereafter, the motor 40 is again activated to position a succeeding extraction tube (H) below the dispensing head and a container (H1) associated with the tube below its nozzle. Thereafter, pump 45 is again activated to dispense the fixed quantity of solvent system into the successively positioned extraction tube. Thus, by succesively positioning each of the extraction tubes below the dispensing head and at each position dispensing the fixed quantity of the solvent system a particular extract from each of the samples in the various extraction tubes is extracted and is automatically transferred in the solvent, in which it is dissolved, to the tube's associated extract container.

Figure 3:
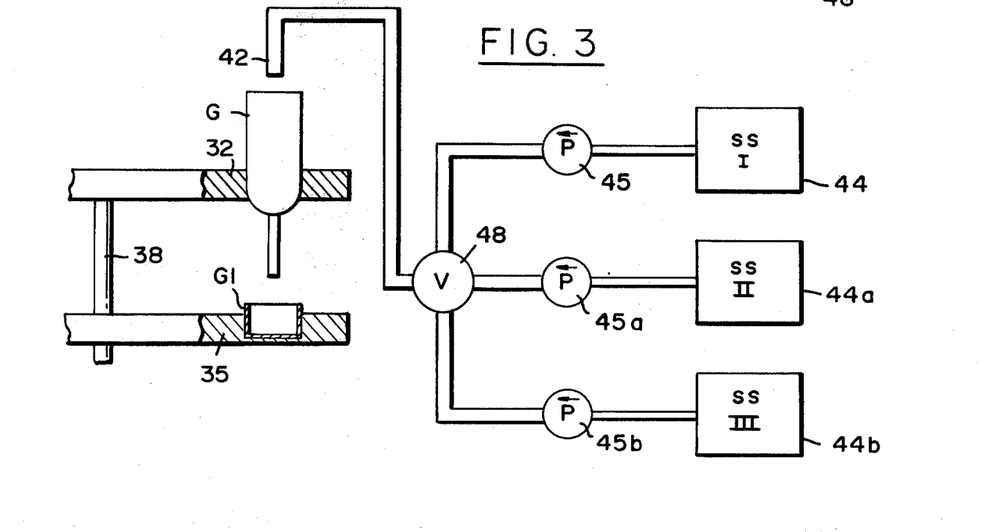

The basic arrangement shown in FIG. 2 may be modified to enable more than one, e.g., three, different extracts to be extracted from each sample and transferred into the single container, associated with the extraction tube in which the sample tube is adsorbed. As shown in FIG. 3, this may be accomplished by adding two more sources 44a and 44b of solvent systems designated SSII, and SSIII respectively, two additional pumps 45a and 45b and a valve 48. The latter is also controlled by unit 46. With such an arrangement after an extraction tube, such as tube G, is positioned below dispensing head 42 pump 45 and valve 48 are activated to dispense the solvent system SSI through head 42 and thereby extract one of the extracts from the sample which is collected in container G1. Thereafter, while the same extraction tube G remains under the head 42, valve 48 is activated as well as pump 45a to dispense solvent system II through the dispensing head into the same extraction tube, and thereby extract a second extract from the sample in the same tube. It should be pointed out that the second extract also exits the nozzle into the same extract container G1, associated with the tube G. This is followed by again activating valve 48 and pump 45b to dispense through dispensing head 42 the fixed quantity of solvent system III, and thereby extract the third extract from the sample in tube G. Again this third extract is also directed to the same extract container G1.

After all the extracts are contained in extract container G1 the motor 40 is activated to position the succeeding extraction tube H below dispensing head 42 and to position container H1 below tube H. Then the whole process is repeated. Thus, in this arrangement each extraction tube is positioned below the dispensing head 42 and in this position three different solvent systems are successively introduced therein to successively extract three different extracts. These are collected in the same extract container associated with the extraction tube.

Figure 4:
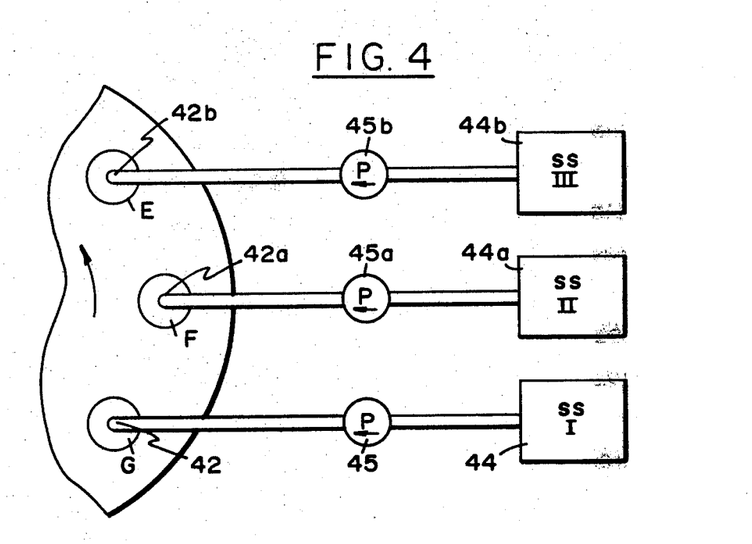

The same results may be obtained by eliminating the valve 48 and incorporating two additional dispensing heads, each connected to a different one of the three pumps and a different one of the three sources, shown in FIG. 3. Such an arrangement is shown in FIG. 4, wherein the two additional dispensing heads are designated by 42a and 42b and are shown connected respectively to pumps 45a and 45b. The three dispensing heads 42, 42a and 42b are positioned so that at each position of the rotatable steppable plate 32 each of the heads is above a different one of three successively positioned extraction tubes, such as extraction tubes G, F and E.

In this arrangement, at each position of the table 32 the three different solvent systems are simultaneously dispensed through the three different dispensing heads into three dispensing extraction tubes. Thus, as each extraction tube is stepped past all three heads, the three solvent systems are successively introduced therein and at each position a different extract is transferred, in the solvent in which it is dissolved, to the extract container with which the extraction tube is associated.

It should thus be appreciated, that after a complete revolution of table 32 three different extracts of each of the samples is present in the extract container associated with the extraction tube in which the sample was originally adsorbed. It should be stressed that with the sample processor of the present invention, only one or more extracts from each sample are extracted while the rest of the sample, which is not of interest, remains adsorbed in the extraction tube. Consequently, it should be apparent that the present invention provides most useful means for extracting particular chemical compounds from each sample for subsequent analysis.

Figure 5:
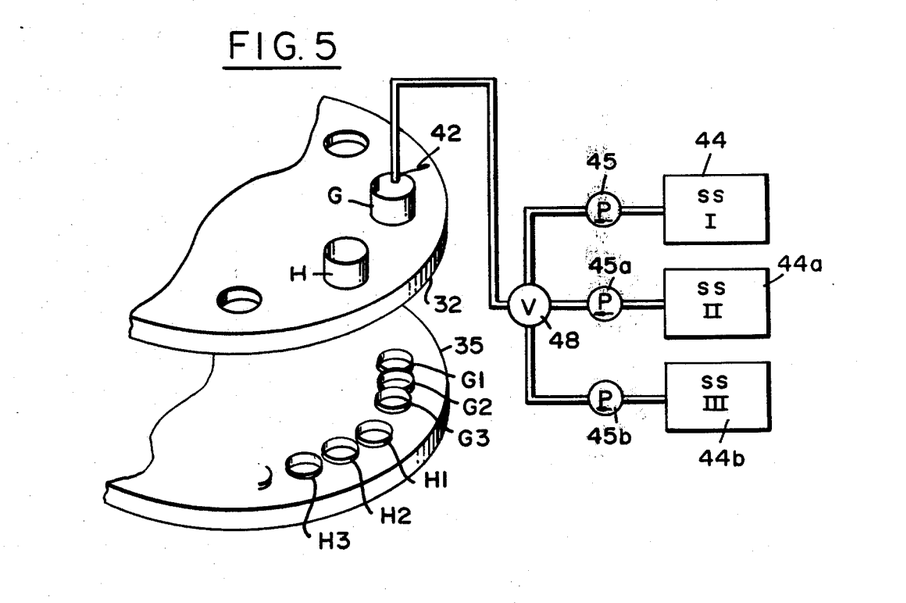

In the embodiments discussed in connection with FIGS. 3 and 4 it is assumed that several extracts from each sample are transferred to a single extract container. If desired or necessary, the sample processor may be modified so that each extract is transferred into a different extract container. For a three extract embodiment each of the extraction tubes may have associated therewith three different extract containers, each used to receive a different solvent dissolved extract. Such an arrangement is shown in FIG. 5, to which reference is made herein. As seen therefrom, supported on plate 35 are three extract containers for each of the extraction tubes. The three containers are designated by the tube's letter designation, e.g., G, followed by the numerals 1, 2, 3, (G1, G2 and G3). The dispensing arrangement is the same as shown in FIG. 3.

In operation, when one of the extraction tubes, e.g., tube G is positioned under the dispensing head 42, plate 35 is stepped so that container G1 is under the extraction tube. In this position solvent system I is dispensed through the head into the extraction tube G and the appropriate extract is directed to container G1. Then only the plate 35 is stepped to position container G2 under extraction tube G. In this position solvent system II is dispensed into extraction tube G and the extract resulting therefrom is directed to container G2. Thereafter, plate 35 is again stepped to position container G3 under the extraction tube followed by the dispensing of solvent system III into the extraction tube, which results in the transfer of the third extract into container G3. Thereafter, both plates are stepped to position a succeeding extraction tube, for example, tube H, under the dispensing head 42 with container H1 associated therewith thereunder. Then, the entire dispensing process is repeated in order to extract three extracts from the sample in tube H and direct each one of the extracts into a different one of the three extract containers H1, H2, and H3, associated with extraction tube H.

This embodiment is similar to the one shown in FIG. 3, except that in the former the three extracts from each sample are directed to a single extract container, while in the embodiment shown in FIG. 5 the three extracts are directed to three separate extract containers. However, in the embodiment of FIG. 5 solvent system dispensing is done only through a single head, so that at any given time only one extract from one sample is extracted.

This limitation may be eliminated by employing a multihead solvent system dispensing arrangement as shown in FIG. 4, and combined with an arrangement in which each extract from each sample is directed and held in a separate extract container. Such an arrangement would greatly speed up the total extraction time from a plurality of samples, since at any given time three extracts from three different samples would be extracted simultaneously.

Figure 6:
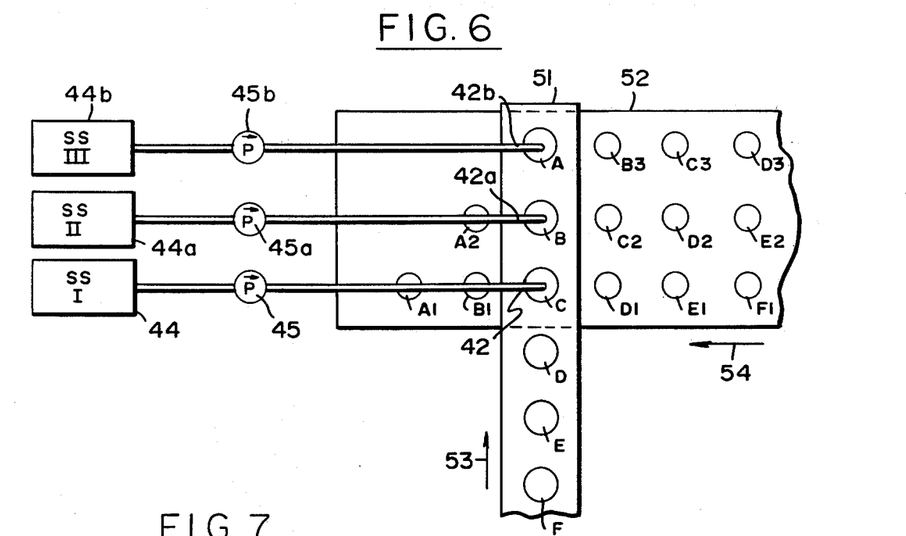

An embodiment capable of such performance is shown in FIG. 6, to which reference is made herein. In this embodiment the extraction tubes as well as the extract containers are shown supported on linearly stepped plates 51 and 52 respectively, rather than on the rotatable steppable plates 32 and 35 as hereinbefore described. Plates 51 and 52 are assumed to be stepped in the directions as represented in FIG. 6 by arrows 53 and 54, respectively. As shown in FIG. 6, extraction tubes C, B and A are assumed to be positioned under dispensing heads 42, 42a and 42b, respectively, and the extract container C1, B2 and A3 which are supported on plate 52 are assumed to be located under the extraction tubes C, B and A.

In this position, solvent systems I, II, and III, are simultaneously dispensed into extraction tubes C, B and A respectively, so that three different extracts are extracted simultaneously from the samples in the three different extraction tubes and directed to three different extract containers, C1, B2 and A3, associated with the three extraction tubes.

Thereafter, both plates 51 and 52 are stepped in the directions represented by the two arrows, thereby causing tubes D, C and B to be located respectively under heads 42, 42a and 42b and at the same time extract containers D1, C2 and B3, are positioned under their respective extraction tubes. Thus, while in the position as shown in FIG. 6, the first extract from the sample in extraction tube C is directed to the extract container C1 located below tube C, in the subsequent position the extract tube C is positioned under the dispensing head 42a and its associated extract container C2 is located thereunder. As a result, the second extract, in response to the dispensing of the solvent system II, is extracted from the sample in the extract tube C and transferred to the extract container C2, associated therewith.

It should thus be apparent, that in this embodiment three different extracts are simultaneously extracted from three different samples into three different extract containers. Consequently, after each extract tube passes past the three dispensing heads the three different extracts, extracted from the sample therein, are separately located in three different extract tubes associated therewith.

In all of the foregoing described embodimentss the one or more extract containers associated with each extraction tube are located below the tube so that each extract as it exits the tube's nozzle, it flows directly into the extract container located below the nozzle. Such embodiments require a separate support structure for the extraction tubes and a different support structure, located thereunder, for the extract containers. If desired, all the tubes and the containers may be located on a single moveable support plate and appropriate plumbing may be employed to direct the extract exiting each tube nozzle to an appropriate container. Such an invention may best be explained first in connection with a simple embodiment in which it is assumed that a single extract is to be extracted from each sample in each of the extraction tubes.

Figures 7, 8:
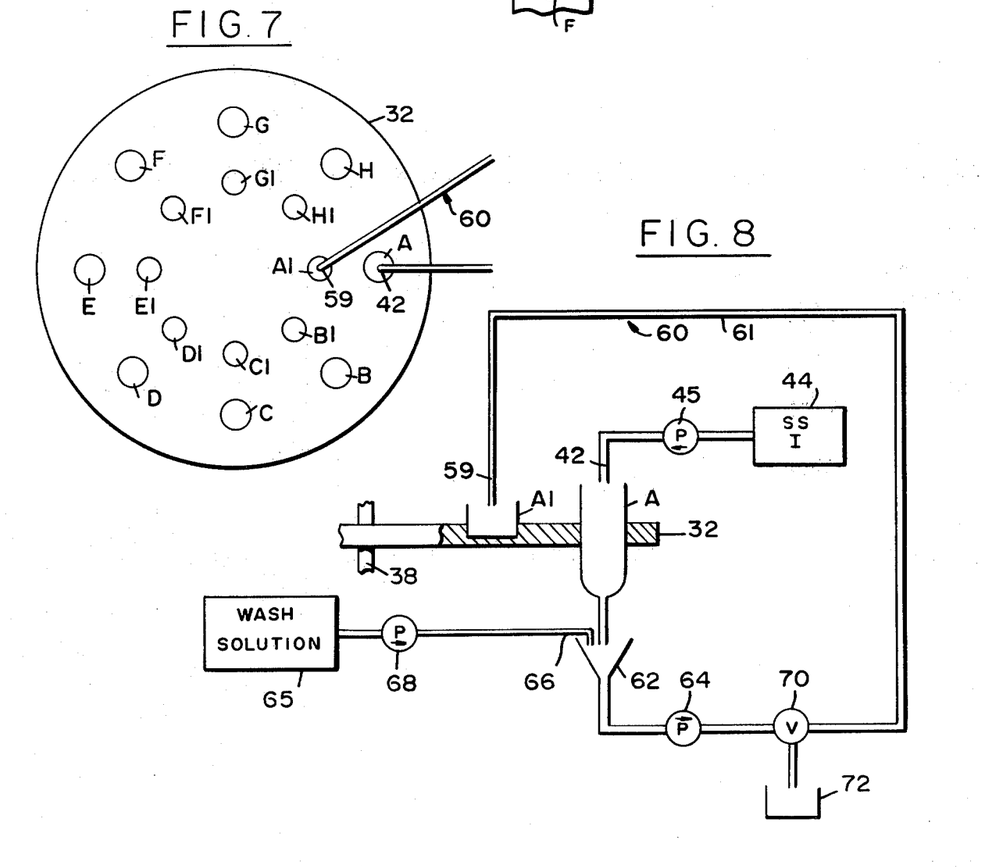
FIGS. 7 and 8 are diagrams of another embodiment of the invention.

A top view and a partial side view of such an embodiment are shown in FIGS. 7 and 8, to which reference is now made. In this embodiment, the extract container, such as A1, associated with extract tube A is radially aligned therewith. In FIGS. 7 and 8 the plate 32 is shown with extract tube A under the dispensing head of 42. In this position the extract container A1 associated with tube A is located underneath end 59 of plumbing arrangement 60 which includes a pipe 61 extending from end 59 to a funnel 62 located below plate 32 and aligned with the dispensing head 42. The plumbing arrangement also incorporates a pump 64. In operation, the extract, extracted from tube A, exits the tube's nozzle and is directed to the funnel 62. Therefrom it is pumped through pipe 61 by means of pump 64 into container A1 through end 59. Thus, the desired extract from the sample in tube A is transferred to its associated extract container A1. Then, the plate 32 is stepped and a succeeding extraction tube and its associated container are respectively positioned under head 42 and open end 59 and the process is repeated.

It should be appreciated that in the present embodiment the plumbing arrangement 60, i.e., pipe 61, funnel 62, and pump 64 are used to communicate each extract extracted from each of the extraction tubes to its associated extract container. Since the same plumbing arrangement is used to communicate extracts from different samples, to prevent cross contamination, it is necessary to cleanse or wash these elements after one extract has passed therethrough before a succeeding extract is to be passed therethrough. This is accomplished in the present embodiment by providing a source 65 of wash solution or simply, wash, which is dispensed into the funnel 62 through a head 66 by means of a pump 68.

In operation, after an extract is extracted from one of the extraction tubes, such as tube A, and is pumped by pump 64 into container A1, pump 68 is activated. It causes a preselected quantity of wash to be dispensed into the funnel 62 through head 66. The function of the wash is to remove any residue of the extract remaining in the funnel and in the pipe 61 and transfer it to container A1 as well as to wash the funnel and the pipe before a subsequent extract is transferred therethrough. The entire dispensed wash solution may be pumped by pump 64 into the container A1. Alternately, the plumbing arrangement may further incorporate a valve 70 which could be operated so that the first portion of the wash solution which may be removing any residue of the extract in the plumbing arrangement is directed therethrough to the appropriate container A1, and the rest of the wash solution, instead of being directed to the extract container, is diverted through valve 70 to a waste container 72. Such an arrangement would reduce the amount of wash which is directed to the extract container.

In practice, the wash from source 65 is a solvent identical to the solvent included in the solvent system. Consquently, by introducing the wash solution into the extract container, which already contains the extract, only the solvent to extract ratio in the container is increased without affecting the extract. By incorporating valve 70 and waste container 72 the amount of solvent, represented by the wash, which is added to the container is minimized and therefore the increase of solvent to extract ratio is less than in the case when all the wash is introduced into container A1.

The last described embodiment with plumbing arrangement 60 may be extended to provide an embodiment similar to the one herebefore described in connection with FIG. 5. Therein three different extracts from three different samples are simultaneously extracted and the three extracts, which are extracted from each sample, are directed and contained in the different extract containers.

Figure 9:
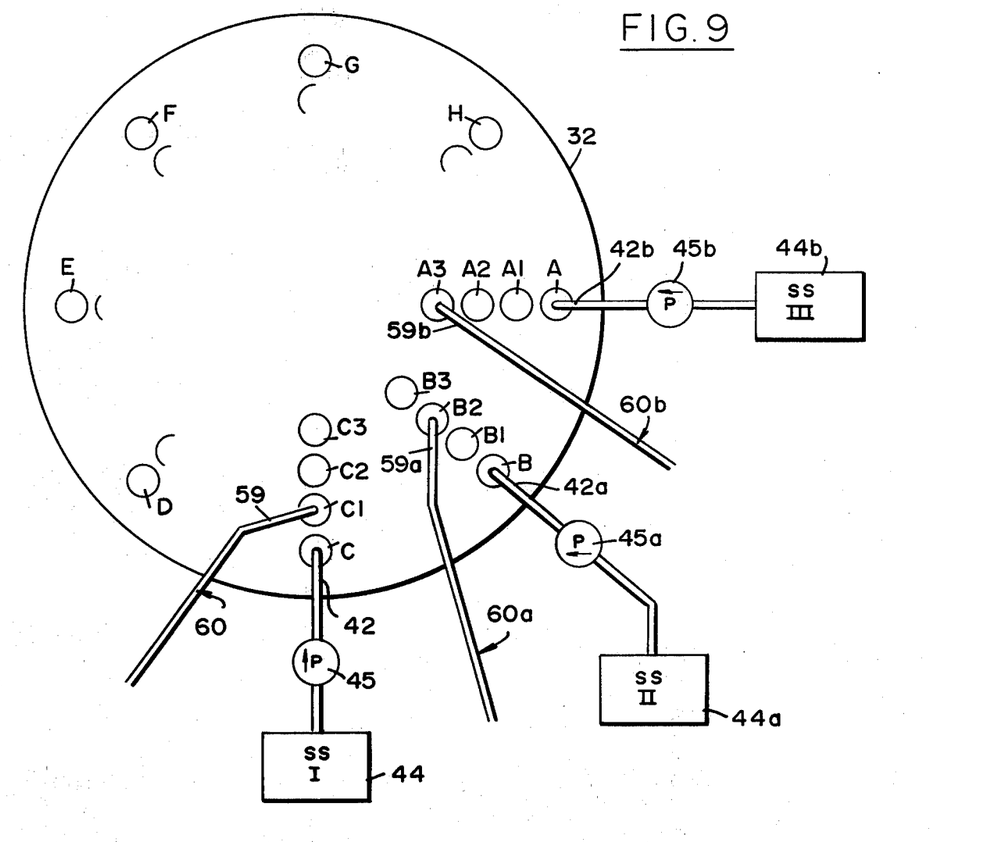
FIG. 9 is a partial diagram of yet another embodiment similar to the one shown in FIGS. 7 and 8.
Figure 10:
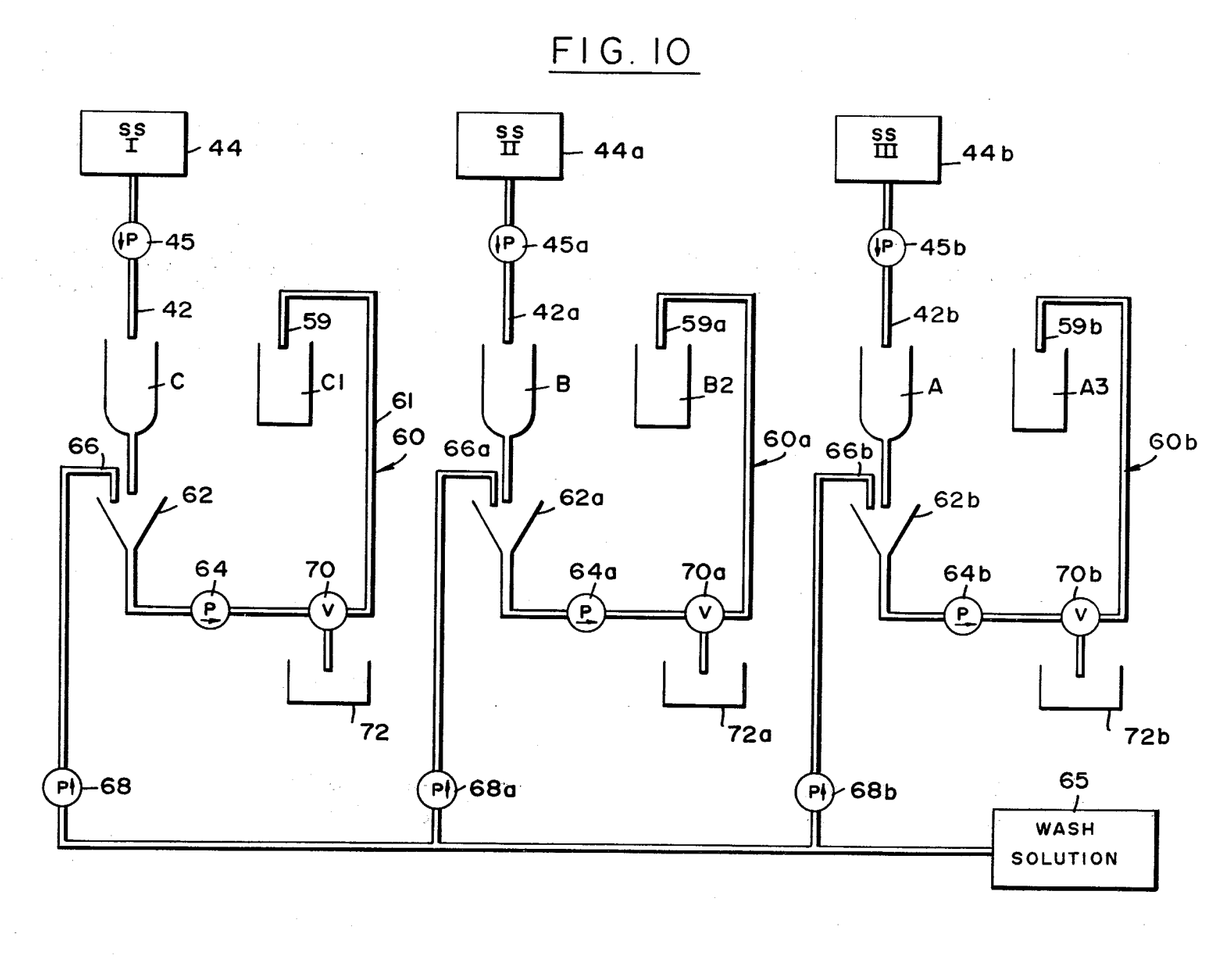
FIGS. 10 and 11 are diagrams useful in explaining yet another embodiment of the invention.

As shown in FIGS. 9 and 10, in this embodiment, three extract containers are associated with each extraction tube and are radially aligned therewith, such as containers A1, A2 and A3 associated with extraction tube A. In FIG. 9 the solvent system dispensing arrangement is similar to that shown in FIG. 4. That is, three different solvent systems from sources 44, 44a, and 44b are simultaneously dispensed by heads 42, 42a and 42b into three successively positioned extraction tubes. Three identical plumbing arrangements like these shown in FIG. 8 are employed. The plumbing arrangements are designated in FIG. 10 by numerals 60, 60a and 60b.

For the position diagrammed in FIG. 9, the extract, exiting extraction tube C, as a result of the injection therein of the solvent system I is pumped through the plumbing arrangement 60, and injected into the extract container C1, while at the same time the extract, exiting extraction tube B in response to the solvent system II, is pumped through plumbing arrangement 60a into extract container B2. Also, at the same time, the extract, which exits extraction tube A in response to the solvent system III, which is injected therein, is pumped through plumbing arrangement 60b and is directed to the extract container A3, associated with tube A.

From the foregoing, it should thus be appreciated that when each extraction tube is positioned adjacent each of the dispensing heads a different solvent system is injected therein and a different extract is extracted from the sample contained therein. Furthermore, the extract is pumped by the plumbing associated with the particular dispensing position to a different one of the three extract containers, associated with the tube. Thus, after a complete revolution of the support plate 32, the three different extracts, extracted from each extraction tube, are present in the three extract containers associated and radially aligned with the tube. It should be stressed that in the last described embodiment, since each plumbing arrangement successively pumps extracts from successive samples, the plumbing arrangement has to be washed before a succeeding extract can be passed therethrough without causing any cross-contamination. It is for this purpose that source 65 of the wash solution and the pumps 68, 68a and 68b (See FIG. 10) are incorporated, to wash each plumbing arrangement after an extract has passed therethrough.

Figure 11:
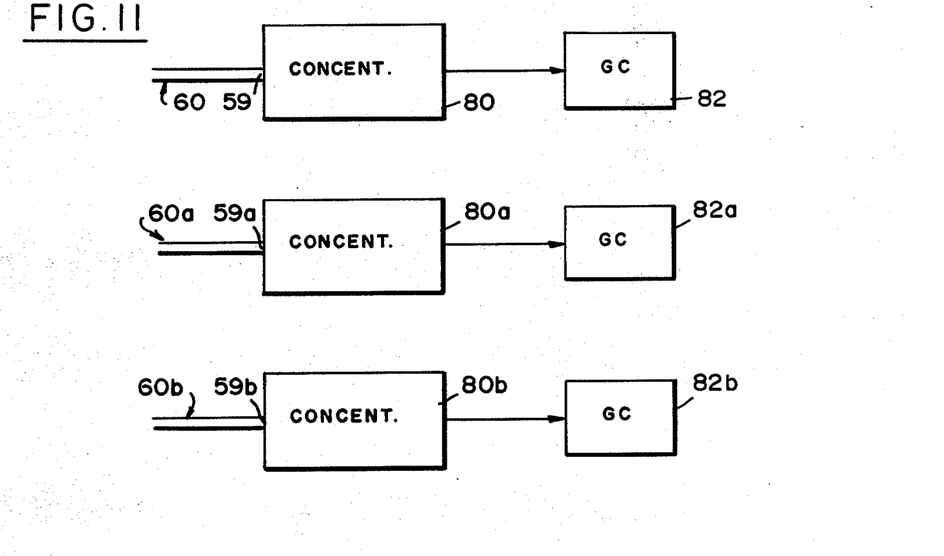

The embodiments which incorporate the plumbing arrangements are particularly adapted for continuous processing of extracts. For example, output end 59 through which successive extracts from the various samples extracted by the solvent system I, instead of being positioned to discharge the various extracts into successively positioned extract container, such as A1, B1, etc., may be connected to an appropriate extract analyzing device which would automatically analyze each extract as it is supplied thereto. For example, as shown in FIG. 11, end 59 may be connected to a concentrator unit 80 which is in turn connected to a gas chromatograph (GC) 82. The function of the concentrator would be to reduce the amount of solvent in which each extract is dissolved to a quantity compatible with that which may be injected or introduced into GC 82. The latter can be operated in a conventional manner to obtain the elution times and thereby identify the various compounds in the extracts in each of the extracts which are successively supplied thereto. Similarly, output ends 59a and 59b of plumbing arrangements 60a and 60b may be connected through concentrators 80a and 80b to two different gas chromatographs 82a and 82b.

The outputs of the three GC's would thus provide significant information about the compounds in the three extracts for each sample for identification or other purposes. By the continuous extract flow from each plumbing arrangement, compounds of different samples may be identified automatically. One such multi-GC system to which the present invention can be applied is described in an article entitled "An Approach to Automated Drug Identification", in the Journal of Forensic Sciences, Volume 16, No. 3, published in July 1971.

Where some form of preprocessing is required prior to extraction, this may be accomplished by incorporation of preprocessing ahead of the extraction stations. For example, hydrolysis of samples, such as urine, may be accomplished by incorporation of a dispensing head connected to a source of a hydrolyzing agent and a heated zone ahead of the extraction stations. Another example is taking samples of volatile vapors from the liquid sample. This may be accomplished by incorporation of a heated zone to volatilize these and a sampling head for their withdrawal from the sample. Several such operations may be accommodated by utilization of separate transport channels, as for example, several sets of circumferential extraction tube holders disposed about the carrousel rotary stepping table with appropriate plumbing and valving to direct the reagents, solvents, and other chemical agents to the appropriate locations.

Figure 12:
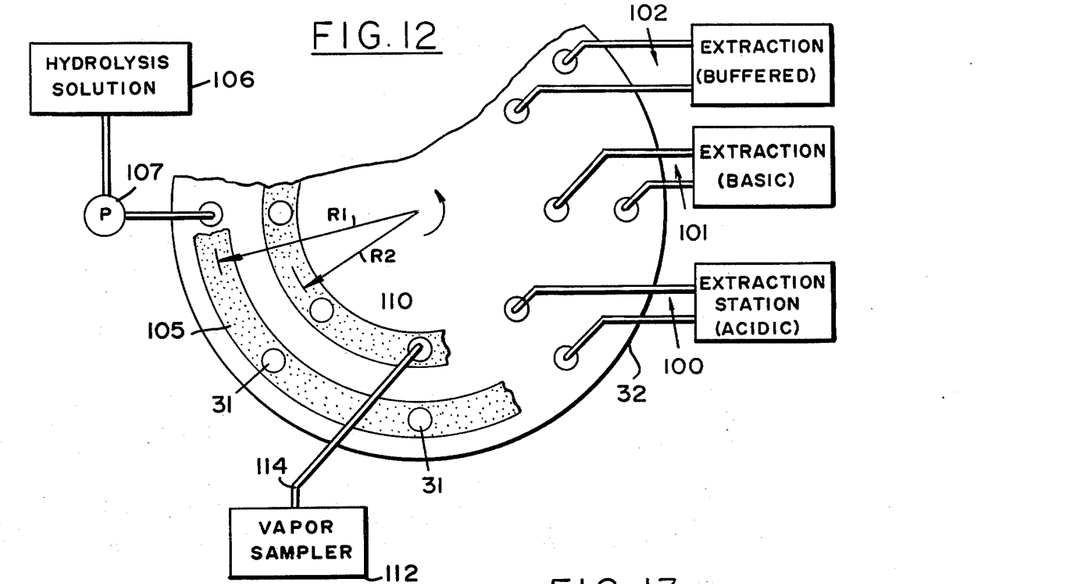
FIGS. 12 and 13 are diagrams useful in explaining an additional capability of the present invention.
Figure 13:
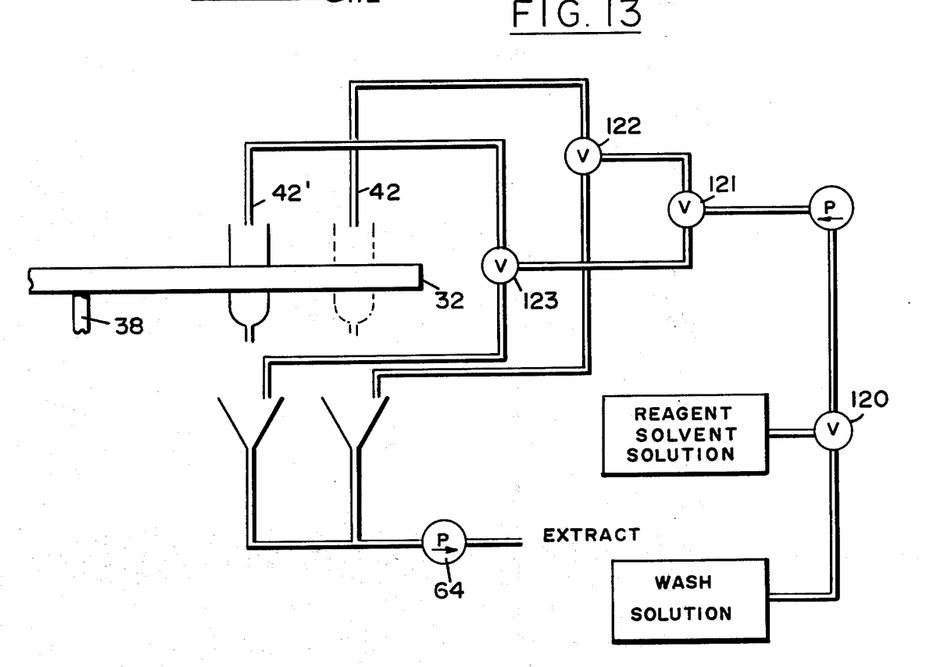

FIGS. 12 and 13 illustrate one such configuration. In these figures it is assumed that samples requiring hydrolysis prior to extractions are placed in openings 31 at a radial distance $R_1$, while those from which headspace samples are to be removed prior to extraction are at a smaller radial distance $R_2$. In FIG. 12, three extraction stations are designated by 100, 101 and 102. A heated zone for hydrolysis represented by lines 105 is provided ahead of the first station 100, so that any sample in a tube at radial distance $R_1$ is heated therein. Ahead of or at the first end of zone 105 is a source 106 of hydrolysis solution and a pump 107. Their function is to pump the hydrolysis solution whenever a tube is located at radial distance $R_1$. Thus, as the tube passes through zone 105 the sample therein is hydrolyzed prior to reaching the first station 100.

Also included is a heated zone 110 for vapor sampling. This tone is used to heat up any sample in a tube at radial distance $R_2$. At the end of zone 110 a vapor sampler 112 is provided to receive, via conduit 114, the vapor (headspace) sample from each tube which passed through zone 110.

As seen from FIGS. 12 and 13, each station, such as station 100, has two dispensing heads, which are analogous to head 42 (FIG. 8). In FIG. 13, they are designated 42 and 42'. Sensors (not shown) are provided to sense whether a tube at station 100 is at radial distance $R_1$ or $R_2$. These sensors activate the various valves 120–123, shown in FIG. 13, to direct the solvent to one of the two heads, depending on the radial distance of the tube thereat. Similarly, these valves are controlled to direct the wash solution to the appropriate funnel.

From the foregoing it should thus be appreciated that in the novel sample processor of the present invention extraction is automatically performed from liquid samples in the extraction tubes. Once the tubes are place on the appropriate support plate the extraction process if fully automatic. Successive extraction tubes are automatically positioned under the dispending heads through which solvent systems are dispensed. The exiting extracts are automatically collected in either the extract containers positioned below the tubes or are pumped through the plumbing arrangements to containers or utilizing devices such as the concentrators and the GC's.

In another application, the concentrated extract may be readied for further analysis by the techniques known as thin-layer chromatography or column chromatography. In yet another application, the concentrated extract may be automatically mixed with a reagent and introduced in a flow through cell for spectrophotometric or fluorometric analysis. Or the concentrated extract may be automatically divided into equal fractions, each specifically treated with a reagent for a multiplicity of anlyses by spectrophotometry of fluorometry.

Although particular embodiments of the invention have been described and illustrated herein, it is recognized that modifications and variations may readily occur to those skilled in the art and consequently it it intended that the claims be interpreted to cover such modifications and equivalents.

What is claimed is:

1. For use in combination with a plurality of discrete separate extraction tubes, each tube comprising a hollow cylinder having an open top end, defining an input end, and an opposite permanently open bottom end, defining a permanently open output end, and packed with packing material between said ends with a liquid sample comprising a plurality of chemical compounds, held in a stationary state on said packing material, a sample processor for successively extracting n different extracts, each comprising a family of compounds from each of said samples, the processor comprising:

tube support means for individually supporting each of said tubes thereon, said tube support means defining apertures in which said tubes are placeable so as to be temporarily supported therein, each tube being removable from said tube support means by merely pulling the tube out of the supporting aperture;

control means for steppingly moving said tube support means so that each of said tubes is successively positioned vertically at a dispensing station;

dispensing means including n sources of different solvent systems, a single dispensing head positioned at said dispensing station above and spaced apart from the input end of any tube positioned thereat, and means for successively dispensing through said dispensing head said solvent systems, whereby as each solvent system is dispensed through said head it gravitationally flows into the tube at said dispensing station through the tube's input end, and as it flows through said tube it extracts from the liquid sample on the packing material in said tube a different extract, representing a different family of compounds, with each of said extracts gravitationally flowing out of said tube through the output end thereof; and receiving means physically separated from said tube support means and said tubes and positionable below the output end of any tube at said dispensing station and spaced apart therefrom and including n separate containers, each having a top open end, associated with each of said extraction tubes, said control means successively stepping said receiving means so that the n containers associated with each tube at the dispensing station are successively positioned below said tube, whereby as each extract gravitationally flows out of the tube at said dispensing station through the tube's permanently open output end the extract flows by gravity directly into a different one of the n containers associated with the tube through the container's top open end, with none of the extracts exiting any of said tubes returning to any of the tubes.

2. The processor as described in claim 1 further including a heated zone through which the extraction tubes, supported on said tube support means, pass for heating the samples therein.

3. The processor as described in claim 2 further including a source of a hydrolysis solution and means for pumping a portion of said hydrolysis solution into extraction tubes prior to entering said heated zone.

4. For use in combination with a plurality of extraction tubes, each tube comprising a hollow cylinder having an open top end defining an input end, and an opposite open bottom end defining a permanently open output end and packed with packing material between said ends with a liquid sample comprising a plurality of chemical compounds in a stationary state on said packing material, a sample processor for extracting n extracts from each liquid sample, each extract comprising a family of compounds, from each of said samples, the processor comprising:

tube support means for supporting said tubes thereon said tube support means being constructed to permit the removal of any tube by the mere application of a pulling force to the tube to be removed;

control means for steppingly moving said tube support means so that each of the tubes is successively positioned vertically at n dispensing stations, said n dispensing stations being spaced apart so that n different tubes are simultaneously positionable at said n stations, n being an integer;

dispensing means including n sources of different solvent systems and n dispensing heads, each head being positioned at a different dispensing station above the input end of any tube positionable thereat and connected to a different one of said sources, each solvent system being of a type whereby when a portion thereof is dispensed through the head to which its source is connected and flows through the tube, positioned below the head, the solvent system extracts a different extract from the liquid sample on the packing material in the tube, with the extract gravitationally flowing out of the tube through the permanently open output end thereof; and receiving means physically separated and spaced apart from said tube support means and said tubes, and positionable below and spaced apart from the open output ends of the tubes at said n stations for receiving by gravitational flow the extracts flowing out of the tubes at said stations, with none of the received extracts returning to any of said tubes.

5. The processor as described in claim 4 wherein said receiving means include n separate removable containers associated with each of said extraction tubes for receiving said n extracts, extracted from the sample in the extraction tube with which the n containers are associated, each of said containers receiving a different one of said extracts.

6. The processor as described in claim 4 further including a heated zone through which the extraction tubes supported on said tube support means pass for heating the samples therein.

7. The processor as described in claim 6 further including a source of a hydrolysis solution and means for pumping a portion of said hydrolysis solution into extraction tubes prior to entering said heated zone.

8. The processor as described in claim 5 wherein said receiving means include container support means for supporting the n containers associated with each of said tubes below the tubes' output ends, and said control means steppingly move said tube support means and said container support means in two linear directions whereby as each tube is successively positioned at each of the n dispensing stations a different one of its associated n containers is below its output end in position to receive one of the extracts flowing out of the tube's output end.

9. The processor as described in claim 8 further including a heated zone through which the extraction tubes supported on said tube support means pass for heating the samples therein.

* * * * *